US010779982B2

(12) United States Patent
Van Meer

(10) Patent No.: US 10,779,982 B2
(45) Date of Patent: Sep. 22, 2020

(54) METHOD FOR DESIGNING AND PRODUCING A CUSTOMIZED DEVICE, THE SHAPE OF WHICH IS ADAPTED TO THE USER'S MORPHOLOGY

(71) Applicant: Anatoscope, Montpellier (FR)

(72) Inventor: Frédérick Van Meer, Perols (FR)

(73) Assignee: Anatoscope, Montpellier (FR)

( * ) Notice: Subject to any disclaimer, the term of this patent is extended or adjusted under 35 U.S.C. 154(b) by 21 days.

(21) Appl. No.: 16/321,335

(22) PCT Filed: Jul. 24, 2017

(86) PCT No.: PCT/FR2017/052034
§ 371 (c)(1),
(2) Date: Mar. 19, 2019

(87) PCT Pub. No.: WO2018/020120
PCT Pub. Date: Feb. 1, 2018

(65) Prior Publication Data
US 2019/0201228 A1    Jul. 4, 2019

(30) Foreign Application Priority Data

Jul. 28, 2016 (FR) ..................................... 16 57263
May 9, 2017 (FR) ..................................... 17 54031

(51) Int. Cl.
*A61F 5/01* (2006.01)
*G06T 7/30* (2017.01)
(Continued)

(52) U.S. Cl.
CPC ........ *A61F 5/0123* (2013.01); *A61F 2/30942* (2013.01); *A61F 2/5046* (2013.01);
(Continued)

(58) Field of Classification Search
CPC ... A61F 5/0123; G05B 19/4099; B33Y 50/00; B29C 33/3835
See application file for complete search history.

(56) References Cited

U.S. PATENT DOCUMENTS 6,236,743 B1   5/2001 Pratt
7,581,953 B2   9/2009 Lehmann et al.
(Continued)

FOREIGN PATENT DOCUMENTS

DE   102005033738   1/2007
EP   0207758 A2     1/1987
(Continued)

OTHER PUBLICATIONS

Van Kaick et al., A Survey on Shape Correspondence, Computer Graphics Forum, vol. 30, No. 6, pp. 1681-1707, Blackwell Publishing Ltd.
(Continued)

*Primary Examiner* — Vincent H Tran
(74) *Attorney, Agent, or Firm* — TraskBritt

(57) ABSTRACT

A method for manufacturing a customized apparatus with a shape adapted to a specific user's morphology, or a mold for such an apparatus, includes obtaining a description of a generic apparatus, or of the mold for such an apparatus, the generic apparatus being adapted to a generic morphology. A description of the generic morphology and a description of the specific user's morphology is obtained. The descriptions of the generic morphology and of the specific user's morphology are processed to identify a geometric transformation mapping together the generic morphology and the specific user's morphology. The geometric transformation is applied to the description of the generic apparatus, or the description of the mold for such apparatus, in order to define (Continued)

the description of the customized apparatus or the mold therefor. The customized apparatus is then manufactured.

8 Claims, 2 Drawing Sheets

(51) Int. Cl.
| | | |
|---|---|---|
| A61F 2/50 | (2006.01) | |
| A61F 2/30 | (2006.01) | |
| G06F 30/00 | (2020.01) | |
| B33Y 50/00 | (2015.01) | |
| B29C 64/386 | (2017.01) | |
| B29C 33/38 | (2006.01) | |
| G05B 19/4099 | (2006.01) | |
| B33Y 80/00 | (2015.01) | |
| B29L 31/00 | (2006.01) | |

(52) U.S. Cl.
CPC ............ *A61F 5/01* (2013.01); *B29C 33/3835* (2013.01); *B29C 64/386* (2017.08); *B33Y 50/00* (2014.12); *G05B 19/4099* (2013.01); *G06F 30/00* (2020.01); *G06T 7/30* (2017.01); *A61F 5/0125* (2013.01); *A61F 2002/505* (2013.01); *A61F 2002/5053* (2013.01); *B29L 2031/757* (2013.01); *B33Y 80/00* (2014.12); *G05B 2219/35134* (2013.01); *G05B 2219/49007* (2013.01); *G06T 2207/30052* (2013.01)

(56) References Cited

U.S. PATENT DOCUMENTS

| | | | |
|---|---|---|---|
| 8,838,263 | B2 | 9/2014 | Sivak et al. |
| 9,358,083 | B2 | 6/2016 | Clausen et al. |
| 2003/0208269 | A1* | 11/2003 | Eaton ................ A61F 2/52 623/7 |
| 2004/0136002 | A1 | 7/2004 | Whaite et al. |
| 2006/0094951 | A1 | 5/2006 | Dean et al. |
| 2006/0235877 | A1* | 10/2006 | Richard ................ G06Q 50/22 |
| 2008/0006273 | A1* | 1/2008 | Thornton ............ B29C 64/386 128/206.21 |
| 2008/0124679 | A1 | 5/2008 | Orth et al. |
| 2009/0157083 | A1 | 6/2009 | Park et al. |
| 2009/0181346 | A1 | 7/2009 | Orth |
| 2012/0063655 | A1 | 3/2012 | Dean et al. |
| 2013/0231911 | A1 | 9/2013 | Brown et al. |
| 2013/0282351 | A1 | 10/2013 | Tank |
| 2015/0178988 | A1 | 6/2015 | Montserrat et al. |
| 2016/0180587 | A1* | 6/2016 | Bai ........................ G06F 30/00 345/419 |
| 2016/0361511 | A9* | 12/2016 | Karpas ................ B33Y 50/02 |
| 2019/0239868 | A1* | 8/2019 | Attenborough .. A61B 17/00491 |

FOREIGN PATENT DOCUMENTS

| | | |
|---|---|---|
| EP | 0913130 A2 | 5/1999 |
| EP | 2363094 A2 | 9/2011 |
| EP | 2496183 | 9/2012 |
| EP | 2661732 | 11/2013 |
| WO | 02/37423 A2 | 5/2002 |
| WO | 2008/145293 A2 | 12/2008 |
| WO | 2011/056995 A2 | 5/2011 |
| WO | 2012/092946 A1 | 7/2012 |
| WO | 2018/020083 A2 | 2/2018 |

OTHER PUBLICATIONS

Sumner et al., Deformation Transfer for Triangle Meshes, Siggraph 2004, Computer Science and Artificial Intelligence Laboratory, Massachusetts Institute of Technology, 7 pages.

Massinissa Bandou, 3D Image Registration & Surface Registration, https://www.youtube.com/watch?v=m_-P8bOKI_0, Published Jan. 29, 2014, 17:18.

James et al., Skinning Mesh Animations, pp. 399-407, Carnegie Mellon University.

Gomes, Warping and Morphing of Graphical Objects, Course Notes, Siggraph 1997, 177 pages.

Europatis Search Report for WO2018020120, dated, Jul. 23, 2018, 5 pages.

Audette et al., An Algorithmic Overview of Surface Registration Techniques for Medical Imaging, Medical Image Analysis (1999), Oxford University Press, 18 pages.

European Communication pursuant to Article 94(3) EPC for European Application No. 17764860, dated Apr. 6, 2020, 4 pages.

Kwok et al., "Domain construction for volumetric cross-parameterization", Computers and Graphics, vol. 38 (Feb. 1, 2014), pp. 86-96.

Meng et al., "Flexible shape control for automatic resizing of apparel products", Computer-Aided Design, vol. 44, No. 1, (2012), pp. 68-76.

Wang et al., "Volume Parameterization for Design Automation of Customized Free-Form Products", IEEE Transactions on Automation Science and Engineering, vol. 4, No. 1 (2007), pp. 11-21.

* cited by examiner

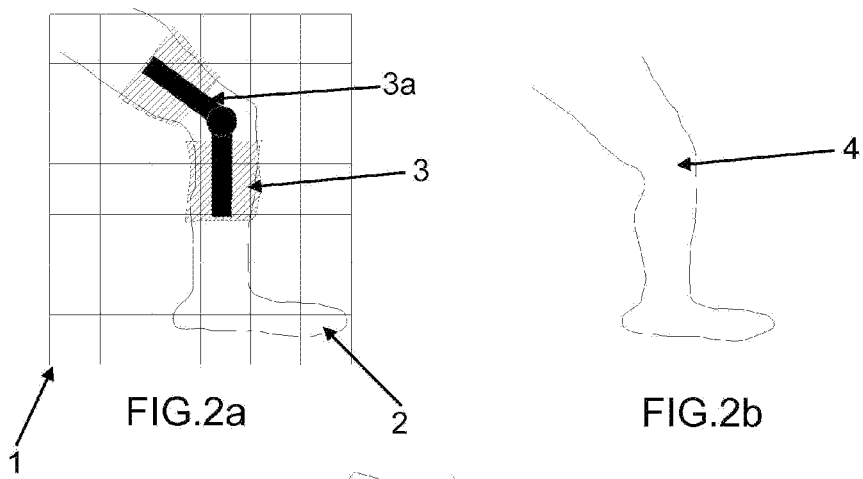
FIG.2a
FIG.2b
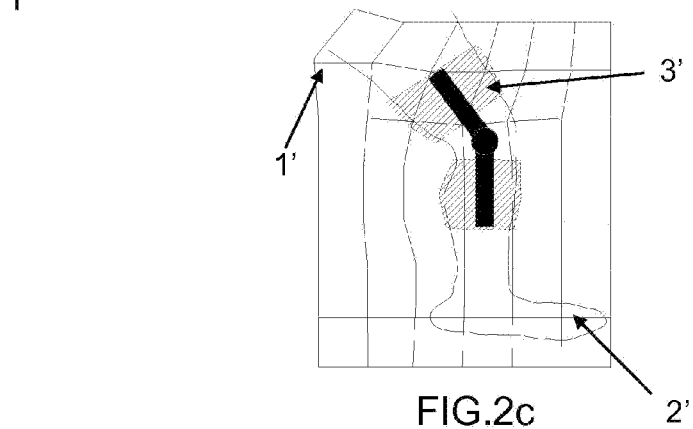
FIG.2c
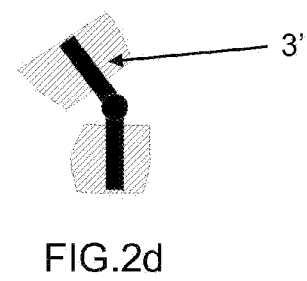
FIG.2d

METHOD FOR DESIGNING AND PRODUCING A CUSTOMIZED DEVICE, THE SHAPE OF WHICH IS ADAPTED TO THE USER'S MORPHOLOGY

CROSS-REFERENCE TO RELATED APPLICATIONS

This application is a national phase entry under 35 U.S.C. § 371 of International Patent Application PCT/FR2017/052034, filed Jul. 24, 2017, designating the United States of America and published as International Patent Publication WO 2018/020120 A2 on Feb. 1, 2018, which claims the benefit under Article 8 of the Patent Cooperation Treaty to French Patent Application Serial No. FR 1657263, filed Jul. 28, 2016, and to French Patent Application Serial No. FR 1754031, filed May 9, 2017.

TECHNICAL FIELD

The present disclosure relates to a method for designing a customized apparatus, or a mold for such apparatus, with the apparatus being adapted to a determined user's morphology to whom it is specifically intended for. The disclosure also relates to a computer program implementing such a design method. The disclosure also relates to a method for producing such apparatus and one apparatus designed and/or manufactured using the methods described.

BACKGROUND

In the context of this disclosure, "apparatus" means any object or device that may be positioned in intimate contact with a user's body. This may be, for example, an object or device the function of which requires it to conform to its user's shape. As a non-exhaustive example of such an object, it may be a medical prosthesis, such as a joint prosthesis like a hip prosthesis, an orthesis such as a knee support or an elbow holder, or any other safety or body protection device such as a helmet, a back support shell, etc. "Mold" refers to any solid body whereon or wherein, for example, a plastic or a resin substance can be applied to copy the shape thereof and form all or part of an apparatus.

For medical, security or safety or comfort reasons, an apparatus is aimed at best adjusting to its user's morphology.

According to a first known design and production method, a material model of a part of the user's body is built, for example, using plaster, foam or wax, that can be obtained directly by molding. This model can then be modified by removing or adding material to obtain a mold, which can then be used to produce the customized apparatus, for example, by thermoforming. This conventional approach is long, expensive and is not suited to the industrial production of customized apparatus.

More recent design approaches of a customized apparatus propose to make a description of the apparatus or its mold rather than making a model. This description may be interpreted by a computer device to make a graphic representation and/or interpreted by production equipment for its actual production. The description may include, for illustration purposes, the decomposition into finite elements by 3D mesh of the surfaces defining the apparatus or its mold.

These recent design approaches can also be based on a description of the user's morphology. This description, similar to that of the apparatus, may include a 3D mesh of the surfaces defining the morphology. Alternatively, or in addition, the description may include a volume image (image composed of voxels) from a measurement device such as an MRI, an X-ray scanner for computed axial tomography, or an ultrasonic measurement device. Alternatively, the description may include a plurality of 2D images (image composed of pixels) taken from different angles, for example, X-rays, allowing the morphology of users to be recomposed.

Such a Computer-Aided design and Computer-Aided Manufacturing (CAD/CAM) solution is, for example, known from the RODIN4D™ software, developed and distributed by the RODIN company.

Thus, according to a known method of designing a customized device, a description of the customized device is developed by combining a first part extracted from the description of the user's morphology and a second part corresponding to a fixed description of the device. The first part corresponds to the surface of the apparatus that is in contact with an area of the user's body, and its shape is defined by conforming to the user's morphology in this area. The second part corresponds to a portion of the apparatus that is not in contact with the user, for example, the external surfaces of the apparatus and, therefore, does not necessarily need customization.

The combination of these two parts, each extracted from a different source, is not easy. In particular, these two parts do not usually connect perfectly, which requires manual editing of the description of the apparatus using a dedicated computer tool. This edition, which aims at making it possible to manufacture the object and erases its imperfections is manual, which makes that design method imperfect, because it is complex and often expensive.

BRIEF SUMMARY

This disclosure is intended to compensate for all or part of the above-mentioned disadvantages. In particular, the present disclosure aims at providing a method for designing and/or producing a customized device that limits or even eliminates the need for manually editing the description of the device.

With a view to achieving at least one of these purposes, the object of the disclosure proposes, according to a first aspect, a method for designing a customized apparatus having a shape that is adapted to a specific user's morphology, or a mold for such an apparatus. The design method includes the following steps:
  obtaining a description of a generic apparatus, or of the mold for such an apparatus, the generic apparatus being adapted to a generic morphology;
  obtaining a description of the generic morphology and a description of the determined user's morphology;
  processing the descriptions of the generic morphology and the determined user's morphology to identify a geometric transformation mapping together the generic morphology and the determined user's morphology match; and
  applying the geometric transformation to the description of the generic apparatus, or the description of the mold for such apparatus, in order to define the description of the customized apparatus or the mold therefor.

According to the other advantageous and unrestrictive characteristics of the disclosure, taken alone or in any technically feasible combination:
  the method involves a preliminary step of measurements to establish the description of the determined user's morphology.

the descriptions include at least one description using a 3D object description language, a 3D mesh, a volume image, or a plurality of 2D images.

the description of the generic apparatus or the mold thereof is associated with local stiffness information so as to locally modulate the application of the geometric transformation during the application step.

According to another aspect, the subject matter of the present disclosure proposes a computer program with instructions adapted to the implementation of each of the steps of the design method, when the program is run on a computer.

According to yet another aspect, the object of the disclosure proposes a method for producing a customized apparatus comprising:

providing a description of the customized apparatus or the mold thereof obtained using the design method proposed; and producing the customized apparatus.

The customized apparatus can be manufactured by additive production or by machining.

The method may include the creation of the mold from the description of the mold for the customized apparatus, for example, by machining or by additive production.

BRIEF DESCRIPTION OF THE DRAWINGS

Other characteristics and advantages of the disclosure will emerge from the detailed description hereunder while referring to the accompanying figures wherein:

FIGS. 2A to 2D show an exemplary embodiment of the method of FIG. 1.

DETAILED DESCRIPTION

Figure 1:
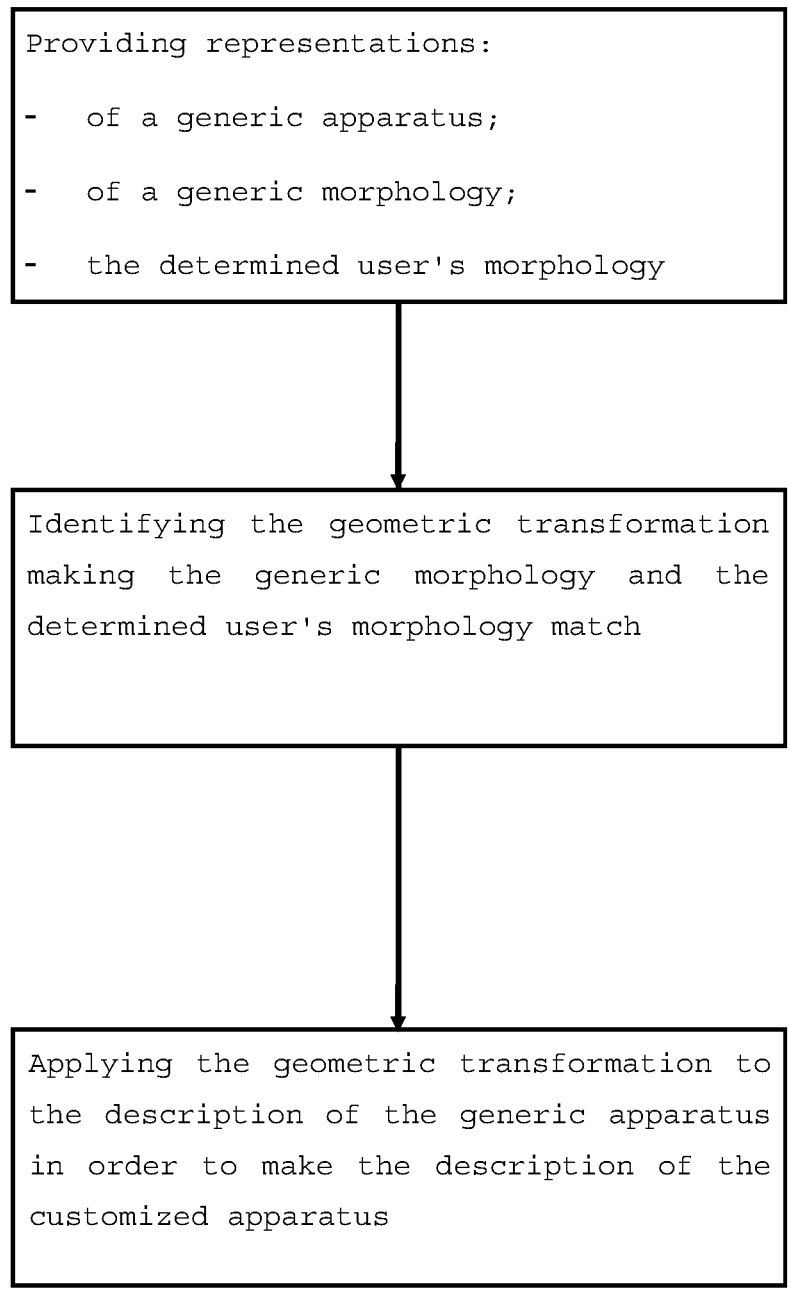
FIG. 1 schematically shows the steps of a method in accordance with the present disclosure.

According to a first aspect, the disclosure relates to a method for designing a customized apparatus, or a mold for such an apparatus, i.e., an apparatus having a shape adapted to a specific user's morphology. It should be noted that this apparatus may be an orthosis or a prosthesis that the determined user wishes to equip himself/herself with.

For the purposes of this description, the term "design" refers to the steps of making a sufficient description of a device (apparatus, mold, etc.), as needed, to enable the representation thereof, for example, in graphical form using computer processing and visualization means or to enable the production thereof. Reference can be made to the general book "Warping & Morphing of Graphical Objects" by J. Gomes, The Morgan Kaufmann Series in Computer Graphics, Morgan Kaufmann, 1998, for a detailed discussion of the well-known methods of description and manipulation of objects.

The disclosure is not limited to a particular form of description of the apparatus, a mold for this apparatus and/or a user's morphology and these descriptions can be formed using an object description language (such as VRML, STL or STEP). They can also be formed by decomposition into finite elements (3D mesh) of the surfaces that define same. They can also be described by a volume image, i.e., composed of points, called "voxels," identified in a three-dimensional space and associated with at least one numerical value that can represent a grayscale or a color. The descriptions of an apparatus or a morphology can also be formed by a plurality of 2D images (composed of "pixels") making it possible to reset the object described in its volume.

A description of an apparatus, a mold, or a morphology can be hybrid, i.e., combine different forms of description such as those just presented. These different forms may relate to identical or complementary parts of the described object.

Whatever the form(s) chosen to describe an object, its description can be materialized by a computer file containing the language elements and/or the pixels, voxels, and/or mesh points that it/they is/are made of.

To design the customized apparatus, this disclosure is based on the availability of a description of a generic device or a mold for this apparatus. The generic apparatus has a form adapted to a user's generic morphology. This generic morphology is itself the subject of a description, referred to in this application as the "description of the generic morphology."

"Generic morphology" refers to a morphology representative of a class of users. Only one generic morphology and the description thereof can be available, and this morphology can then constitute an average and simplified morphology of a human body. Alternatively, a plurality of generic morphologies (and the descriptions thereof) may be available, for example, a male generic morphology and a female generic morphology. In all cases, a generic morphology and the description thereof form a representative, albeit simplified, version of the class of users it represents. It should be noted that it is not necessary for the description of the generic morphology to represent an entire human body. This may be the most relevant part of this body relative to the apparatus under consideration.

A generic morphology, and the representation thereof, is associated with a description of a generic apparatus, or a description of a mold for such an apparatus. The generic apparatus is precisely adapted to the generic morphology, i.e., the surfaces that will be, in operation, in contact with the user complying with the generic morphology. Of course, the generic morphology and the apparatus generic are described in the same starting space, which makes it possible to associate the same with each other, to identify the same relative to each other, and to ensure that they are well tailored to each other.

Since the generic morphology is generally a simplified representation of a real morphology, it is clear that this generic apparatus or the mold thereof are easily described.

To design the customized apparatus, the disclosure is also based on the availability of a description of the determined user's morphology to whom the customized apparatus is intended for.

As seen above, this description can take multiple and hybrid forms, but advantageously the description results from a measurement system of the I.R.M. type, or from an X-ray scanner for computed axial tomography, or from an ultrasonic measurement device. These means make it possible to obtain very directly a volume image of the user's morphology. Alternatively, the description can be obtained from a measurement system to obtain a plurality of 2D images of the user. It can be an X-ray device. In yet another alternative embodiment, the description can be obtained from a skin surface measurement system. It can be a depth camera or laser scanning.

The description of the specified user's morphology or a complete description of this user's body need not be complete, and only the part of his/her body most relevant to the apparatus to be produced may be sufficient.

FIG. 1 schematically shows the steps of a method in accordance with a first embodiment of the disclosure. The method includes a first series of steps consisting in, without any imposed order, obtaining the representation of an apparatus having a shape that is adapted to a generic morphology, obtaining a description of this morphology and obtaining a description of the determined user's morphology. Descriptions of the generic apparatus and generic morphology can be derived from, and chosen from, one previously constituted library. In the event that one does not have a description of the determined user's morphology, this sequence of steps can include or be preceded by a step aiming at making this representation. This may be, for example, but not exclusively, one of the measurement techniques presented above.

In a subsequent step, the method according to the disclosure includes a step of processing the description of the generic morphology and the description of the identified user's morphology. Such processing identifies the geometric transformation of the space by matching the generic morphology, defined and described in a starting space, and the determined user's morphology, defined and described in an end space.

Such processing operations are well known to the person in the art, as shown in J. Gomes' book cited above. Reference may also be made to the review articles by M. A. Audette, F. P. Ferrie, and T. M. Peters (2000), "An algorithmic overview of surface registration techniques for medical imaging," *Medical image analysis*, 4(3), 201-217; or O. Van Kaick, H. Zhang, G. Hamarneh, and D. Cohen-Or (2011, September), "A survey on shape correspondence," in *Computer Graphics Forum* (Vol. 30, No. 6, pp. 1681-1707), Blackwell Publishing Ltd., for a detailed overview of existing algorithms and techniques that can be applied.

In a very general way, this processing comprises determining the transformation of the space that best matches the elements defining a first description of an object in a first position with elements defining a second description of that object in a second position. This processing is generally considered as an optimization problem, the solving of which uses known function-minimizing techniques, for example, derived from a gradient method. This disclosure uses known object description-matching algorithms to identify the geometric transformation matching the generic morphology with the determined user's morphology.

This geometric transformation can be indifferently applied to the representation of the generic morphology to obtain the determined user's morphology. Conversely, it may be the one applied to the description of the determined user's morphology to obtain a morphology best matching that of the generic morphology. In this last case, great care is taken to reverse the geometric transformation before applying it in accordance with the next step of the design method, the description of which is given hereunder.

The geometric transformation can be determined as a combination of translation, rotation, homothety, etc.

More generally, the geometric transformation can be a deformation field associating, for example, each point of the starting space with a point of the end space; or associating a displacement to be applied in the X, Y and Z directions at each point of the starting space to determine the point of the end space.

In a subsequent step of the method according to the disclosure, the geometric transformation identified with the description is applied to the generic apparatus to make the description of the customized apparatus.

By applying the same transformation to the description of the generic apparatus as those matching the generic morphology and the specific user's morphology, the customized apparatus is assuredly adapted to the specific user's morphology. As the transformation applies to the space containing the apparatus as a whole (e.g., by applying the identified deformation field, as previously specified), it is not necessary to combine several parts together to make the description of the customized apparatus. The need for manually editing the description of the customized apparatus is thus limited, or even eliminated.

In a particular embodiment of the disclosure, the step of applying the geometric transformation is implemented concurrently with the step of determining the geometric transformation.

According to a particularly advantageous embodiment, the description of the generic apparatus is associated to local information on rigidity. This information specifies which areas of the generic apparatus can be freely transformed or deformed, those that must not be transformed or deformed, or those that must undergo a lower degree of transformation or deformation. The application of the geometric transformation to the generic apparatus can thus be locally modulated. This may have the advantage of preserving, in the adapted apparatus, portions that have not fully undergone geometric transformation and can, therefore, preserve, at least in part, the original geometry thereof. These may be functional portions of the apparatus, such as a joint, that could be rendered inoperative by a poorly controlled transformation.

Following the implementation of the design method just presented, a description of the appropriate apparatus is, therefore, available. This description, in particular, when it takes the form of a computer file, may be used as such by processing and/or visualization devices, for example, to constitute objects integrated in an animated sequence.

FIGS. 2A to 2D represent an exemplary application of a method in accordance with the disclosure to the design of a leg orthosis.

FIG. 2A represents, in a starting space materialized by the grid 1, a generic morphology 2 of a user's limb and the generic orthosis 3 associated with such limb. A functional, "rigid," part 3a of the orthosis has also been represented, which must not be transformed. The representation of the morphology and the orthosis was obtained from their descriptions, which define these objects in three dimensions. This description also defines the degree of rigidity of the functional part 3a, as described above. One could have chosen to represent the orthosis and morphology from another angle, or to represent them separately. The descriptions that both representations are based on may have been specifically designed or extracted from a pre-existing library.

FIG. 2B shows, from the same angle of view as the one used in FIG. 2A, a morphology 4 of a specific user's limb, for example, obtained by a 3D scanning technique. Similar to the comments applying to FIG. 2A, the representation of the determined user's morphology was obtained from the description thereof, which defines this object in three dimensions.

FIG. 2C represents the geometric transformation applied to the generic morphology 2 to match it with the determined user's morphology 4. This transformation is notably materialized by the deformation of the grid 1', defining the deformation field applying to the starting space to ensure this correspondence. It can be seen that the morphology 2' shown in this figure is very similar to the determined user's morphology 4 shown in FIG. 2B.

This FIG. 2C also shows the generic orthosis 3, which the same transformation field has been applied to as the one applied to the generic morphology, to form the transformed generic orthosis 3'. This transformed orthosis 3' defines the orthosis adapted to the particular user, which is represented in FIG. 2D.

According to a second embodiment of the present disclosure, the design method aims at creating a mold for the customized apparatus rather than the apparatus itself.

The implementation of the mold design method is entirely similar to the one described in relation to the first embodiment. For the sake of conciseness, this description is therefore not repeated, but applies in full.

In the case of this second embodiment, the method includes a step of obtaining a description of the mold used to make the generic apparatus.

Then, the geometric transformation of the space that matches the generic morphology with the determined user's morphology is applied to the mold for the generic apparatus in order to obtain the description of the mold for the customized apparatus.

Once manufactured, this mold makes it possible to produce, for example, by thermoforming, the customized apparatus.

The design method according to the disclosure is intended to be implemented by a computer, through a computer program consisting of instructions adapted to implement at least each of the steps of this method.

According to another aspect of the disclosure, the description of the customized apparatus is used to produce the customized apparatus as such or the mold thereof, so that it can equip the determined user. According to this other aspect, the disclosure thus relates to a method for producing a customized apparatus or its mold. It also relates to the customized apparatus obtained using this method.

Advantageously, the customized apparatus or its mold is obtained by additive production, particularly well adapted to the manufacture of a single object, as is the case for a user-tailored apparatus. It can also be manufactured by machining.

The invention claimed is:

1. A method for manufacturing a customized apparatus with a shape adapted to a specific user's morphology or a mold for the customized apparatus, the method comprising the following steps:
   receiving data relating to a 3D digital model of a generic apparatus or a physical mold for the generic apparatus, the generic apparatus being adapted to a generic morphology;
   receiving data relating to a 3D digital model of the generic morphology;
   receiving data relating to a 3D digital model of the specific user's morphology;
   analyzing the data relating to the 3D digital model of the generic morphology and the data relating to a 3D digital model of the specific user's morphology using a computer to determining a geometric transformation mapping the generic morphology to the specific user's morphology;
   applying the determined geometric transformation to the data relating to the 3D digital model of the generic apparatus or the mold for the generic apparatus and generating a 3D digital model of the customized apparatus or a mold for a customized apparatus; and
   manufacturing the customized apparatus or the mold for the customized apparatus.

2. The method of claim 1, wherein receiving data relating to a 3D digital model of the specific user's morphology comprises measuring at least a portion of a body of the user.

3. The method of claim 1, wherein the data relating to each of the 3D digital models comprises at least one of computer code in a 3D object description language, a 3D mesh, a volume image, or a plurality of 2D images.

4. The method of claim 1, wherein the data relating to the 3D digital model of the generic apparatus or the mold of the generic apparatus is associated with data relating to local stiffness information, and wherein applying the determined geometric transformation to the data relating to the 3D digital model of the generic apparatus or the mold for the generic apparatus comprises locally modulating the application of the geometric transformation using the data relating to local stiffness information when creating the 3D digital model of the customized apparatus or the mold for the customized apparatus.

5. The method of claim 4, wherein manufacturing the customized apparatus or the mold for the customized apparatus comprises using an additive manufacturing process or a machining process.

6. The method of claim 4, wherein:
   the method comprises a method for manufacturing a mold for a customized apparatus having a shape adapted to a specific user's morphology;
   receiving data relating to the 3D digital model of the generic apparatus or of the mold for the generic apparatus comprises receiving data relating to the 3D digital model of the mold for the generic apparatus;
   applying the determined geometric transformation to the data relating to the 3D digital model of the generic apparatus or the mold for the generic apparatus and generating a 3D digital model of the customized apparatus or the mold for the customized apparatus comprises applying the determined geometric transformation to the data relating to the 3D digital model of the mold for the generic apparatus and generating a 3D digital model of the mold for the customized apparatus; and
   manufacturing the customized apparatus or the mold for the customized apparatus comprises manufacturing the mold for the customized apparatus.

7. The method of claim 6, wherein manufacturing the mold for the customized apparatus comprises using an additive manufacturing process or a machining process.

8. A computer system configured under control of a program to perform the following processes:
   receive and store a 3D digital model of a generic apparatus or a mold for the generic apparatus, the generic apparatus being adapted to a generic morphology;
   receive and store a 3D digital model of the generic morphology receive and store a 3D digital model of a specific user's morphology;
   analyze the 3D digital model of the generic morphology and of the 3D digital model of the specific user's morphology to determine a geometric transformation mapping the generic morphology to the specific user's morphology; and
   apply the determined geometric transformation to the 3D digital model of the generic apparatus; or the mold for the generic apparatus, to define a 3D digital model of a customized apparatus or a mold therefor.

* * * * *